US009629596B2

(12) United States Patent
Taguchi et al.

(10) Patent No.: US 9,629,596 B2
(45) Date of Patent: Apr. 25, 2017

(54) X-RAY CT APPARATUS AND IMAGE PROCESSING METHOD

(75) Inventors: Hiroki Taguchi, Otawara (JP); Masaharu Tsuyuki, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 298 days.

(21) Appl. No.: 13/614,341

(22) Filed: Sep. 13, 2012

(65) Prior Publication Data
US 2013/0010922 A1 Jan. 10, 2013

Related U.S. Application Data

(63) Continuation of application No. PCT/JP2011/077548, filed on Nov. 29, 2011.

(30) Foreign Application Priority Data

Nov. 29, 2010 (JP) ................... 2010-265596

(51) Int. Cl.
*A61B 6/03* (2006.01)
*G06K 9/36* (2006.01)
*A61B 6/00* (2006.01)

(52) U.S. Cl.
CPC ............ *A61B 6/488* (2013.01); *A61B 6/032* (2013.01); *A61B 6/481* (2013.01); *A61B 6/54* (2013.01)

(58) Field of Classification Search
CPC ......... A61B 6/032; A61B 6/481; A61B 6/488; A61B 6/54

(Continued)

(56) References Cited

U.S. PATENT DOCUMENTS 6,188,744 B1 2/2001 Shinohara et al.
2003/0108149 A1 6/2003 Tsuyuki
(Continued)

FOREIGN PATENT DOCUMENTS

JP 2624927 4/1997
JP 11-342125 A 12/1999
(Continued)

OTHER PUBLICATIONS

English translation of the International Preliminary Report on Patentability and Written Opinion of the International Searching Authority issued Jan. 17, 2012, in PCT/JP2011/077548, filed Nov. 29, 2011.

(Continued)

*Primary Examiner* — Dani Fox
(74) *Attorney, Agent, or Firm* — Oblon, McClelland, Maier & Neustadt, L.L.P.

(57) ABSTRACT

An X-ray CT apparatus has a scanner, a pre-scan control unit, an image generating unit, a region setting unit and a timing sensing unit. The pre-scan control unit controls an operation of the scanner to perform a pre-scan. The image generating unit generates image data of the object based upon the pre-scan. The region setting unit sets, on the basis of the image data, a region of interest, and a larger region encompassing the region of interest and a region around the region of interest and being used to determine whether or not a high pixel value region exists. The timing sensing unit senses, if the larger region does not include a pixel value higher than a first threshold, a timing to start a main scan, at which a pixel value of the region of interest exceeds a second threshold after injection of the contrast medium agent is started.

14 Claims, 8 Drawing Sheets

(58) Field of Classification Search
USPC .......................................................... 378/19
See application file for complete search history.

(56) References Cited

U.S. PATENT DOCUMENTS

2009/0022265 A1    1/2009  Takase et al.
2010/0292570 A1*  11/2010  Tsukagoshi .................. 600/431

FOREIGN PATENT DOCUMENTS

| JP | 2003-245275 A | 9/2003 |
| JP | 2009-022455 A | 2/2009 |

OTHER PUBLICATIONS

International Search Report issued Jan. 17, 2012 in PCT/JP2011/077548 filed Nov. 29, 2011.

* cited by examiner

X-RAY CT APPARATUS AND IMAGE PROCESSING METHOD

CROSS-REFERENCE TO RELATED APPLICATION

This application is a Continuation Application of No. PCT/JP2011/077548, filed on Nov. 29, 2011, and the PCT application is based upon and claims the benefit of priority from Japanese Patent Application No. 2010-265596, filed on Nov. 29, 2010, the entire contents of which are incorporated herein by reference.

FIELD

The present embodiment as an aspect of the present invention relates to an X-ray CT (computed tomography) apparatus and an image processing method in which a contrast medium agent is injected into an object and a scan is performed.

BACKGROUND

Conventionally, X-ray CT apparatuses have increasingly carried out tomography called the dynamic scan. The dynamic scan is a technique for, after a contrast medium agent is administered, continuously performing scans over a predetermined time period depending upon a rate of the contrast medium agent flowing through an object.

A conventional X-ray CT apparatus generates a non-contrast image of an object in non-contrast, sets an ROI (region of interest) and a threshold based on the non-contrast image, and starts the injection of a contrast medium agent. After the start of the injection of the contrast medium agent, Real Prep starts. Real Prep is a function for sensing a timing of start (trigger) for a main scan such as a dynamic scan and starting the main scan when a CT value of the ROI exceeds the threshold.

In conventional ROI setting, merely an operator places an ROI on any position using a non-contrast image. Currently, however, Real Prep is used in various situations. For example, Real Prep is carried out while a patient is breathing, or a main scan is immediately performed once a contrast medium agent reaches a predetermined region. Furthermore, it is necessary to sense a timing to start a main scan with high accuracy. However, in the conventional arts, there is the case in which even if a high CT value region such as a bone or a calcified area is outside and around an ROI at the time of ROI setting that uses a non-contrast image, after Real Prep is started, the high CT value region may enter the ROI because of a heartbeat, breathing, or a body movement of an object. As a result, a timing to start a main scan may be mistaken.

A body movement of an object often involves up-and-down motions as well as forward, backward, right and left motions. Further, if Real Prep is carried out near a main artery aorta while an object is breathing, it is likely that up-and-down motions of the object cause a high CT value region such as a calcified area to enter an ROI.

BRIEF DESCRIPTION OF THE DRAWINGS

In accompanying drawings.

DETAILED DESCRIPTION

Figure 1:
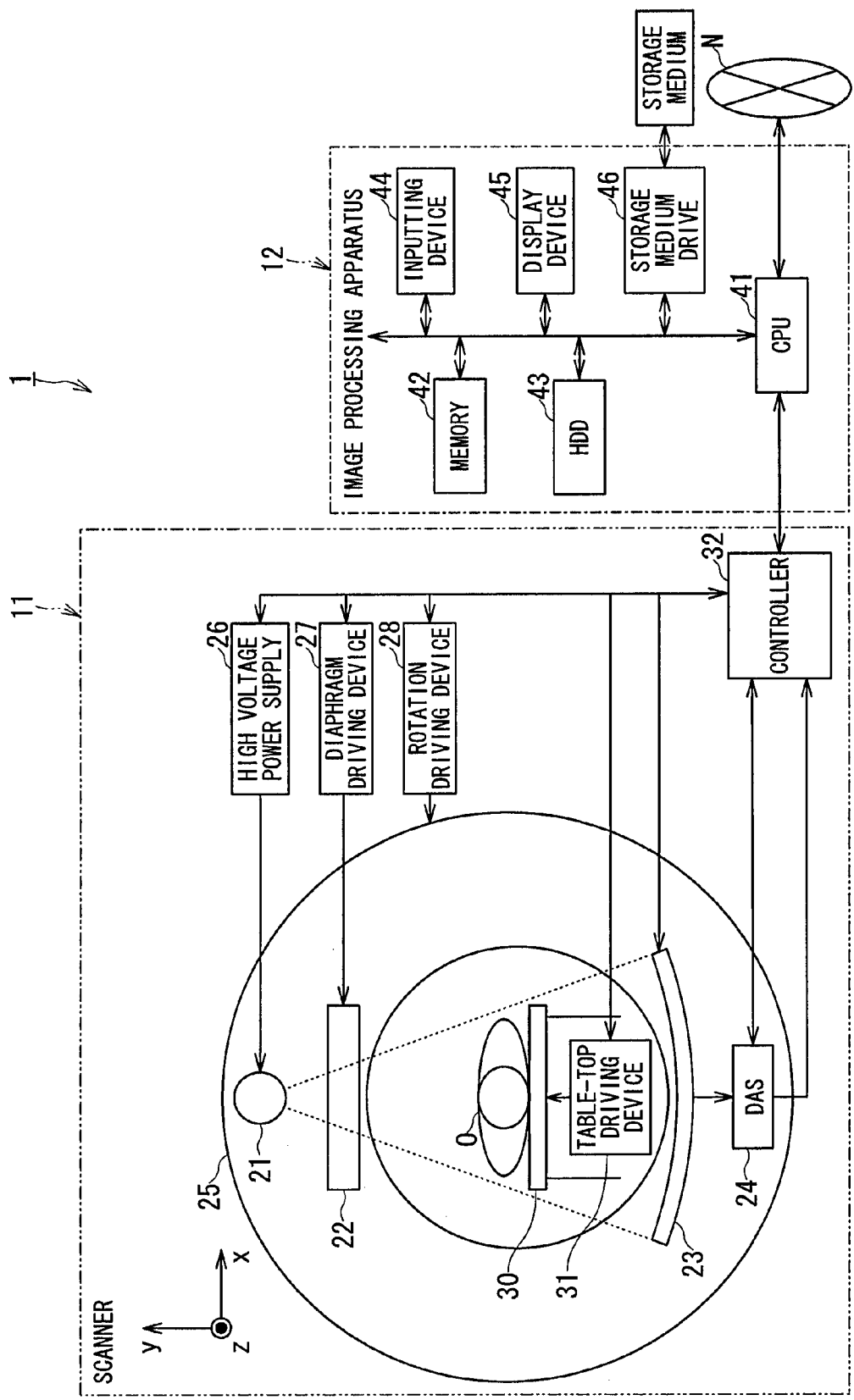
FIG. 1 is a block diagram illustrating an X-ray CT apparatus according to the present embodiment.

An X-ray CT apparatus and an image processing method of the present embodiment will be described with reference to the accompanying drawings.

To solve the above-described problems, the present embodiments provide the X-ray CT apparatus includes: a scanner configured by an X radiation source and an X-ray detector and to collect data of an object; a pre-scan control unit configured to control an operation of the scanner to perform a pre-scan; an image generating unit configured to generate image data of the object based upon the pre-scan; a region setting unit configured to set, on the basis of the image data, a region of interest for measurement of variation of a contrast medium agent, and a larger region encompassing the region of interest and a region around the region of interest and being used to determine whether or not a high pixel value region exists; and a timing sensing unit configured to sense, if the larger region does not include a pixel value higher than a first threshold, a timing to start a main scan, at which a pixel value of the region of interest exceeds a second threshold after injection of the contrast medium agent is started.

To solve the above-described problems, the present embodiments provide the image processing method includes: performing a pre-scan by controlling an operation of a scanner configured by an X radiation source and an X-ray detector and to collect data of an object; generating image data of the object based upon the pre-scan; setting, on the basis of the image data, a region of interest for measurement of variation of a contrast medium agent, and a larger region encompassing the region of interest and a region around the region of interest and being used to determine whether or not a high pixel value region exists; and sensing, if the larger region does not include a pixel value higher than a first threshold, a timing to start a main scan, at which a pixel value of the region of interest exceeds a second threshold after injection of the contrast medium agent is started.

The X-ray CT apparatus of the present embodiment includes a variety of types such as a rotation/rotation type in which an X radiation source and an X-ray detector rotate around a object as an integrated unit and a stationary/rotation type in which a large number of detecting elements are arrayed in a ring form and only an X radiation source rotates around a object, and any one of the types can be applied to the present invention. Herein, the rotation/rotation type, which is in the mainstream, will be described.

A dominating mechanism for converting incident X-rays into an electric charge includes indirect conversion in which X-rays are converted into light with a fluorescent substance such as a scintillator and the light is further converted into an electric charge with a photoelectric transducer such as a photodiode, and direct conversion by means of generation of electron-hole pairs in a semiconductor by X-rays and their migration to an electrode, namely, a photoconductive phenomenon.

Additionally, what is called multi-tubular X-ray CT apparatuses in which a plurality of pairs of an X radiation source and an X-ray detector are mounted on a rotation ring has become commercially available in recent years, and related techniques of the multi-tubular X-ray CT apparatuses have been developed. The X-ray CT apparatus of the present embodiment may be applied to any of the conventional single-tubular X-ray CT apparatuses and the multi-tubular X-ray CT apparatuses. Herein, a single-tubular X-ray CT apparatus will be described.

FIG. 1 is a block diagram illustrating the X-ray CT apparatus according to the present embodiment.

FIG. 1 illustrates an X-ray CT apparatus 1 that performs a scan by injecting a contrast medium agent into an object in accordance with the present embodiment. The X-ray CT apparatus 1 mainly includes a scanner 11 and an image processing apparatus 12. The scanner 11 of the X-ray CT apparatus 1 is typically installed in an examination room and generates X-ray transmission data associated with a patient (object) O. The image processing apparatus 12 is typically installed in a control room adjacent to the examination room and generates projection data based on the transmission data to generate and display a reconstruction image.

The scanner 11 of the X-ray CT apparatus 1 includes an X-ray tube (X radiation source) 21, a diaphragm 22, an X-ray detector 23, a DAS (data acquisition system) 24, a rotation portion 25, a high voltage power supply 26, a diaphragm driving device 27, a rotation driving device 28, a table-top 30, a table-top driving device 31, and a controller 32.

The X-ray tube 21 generates an electron beam to collide with a metal target depending upon a tube voltage supplied from the high voltage power supply 26 to generate X-rays, and applies the X-rays to the X-ray detector 23. Fan beam X-rays and cone beam X-rays are formed by the X-rays applied from the X-ray tube 21. The X-ray tube 21 is supplied with power required to apply X-rays in response to control of the controller 32 through the high voltage power supply 26.

The diaphragm 22 adjusts, by way of the diaphragm driving device 27, an irradiated range of X-ray irradiated from the X-ray tube 21 in a slice direction and a direction normal to the slice direction. That is, by adjusting an aperture of the diaphragm 22 by the diaphragm driving device 27, an irradiated range of X-ray in the slice direction and the direction normal to the slice direction can be changed.

The X-ray detector 23 is a one-dimensional array type detector (also referred to as a single-slice type detector) having a plurality of detecting elements in a channel direction and a single detecting element in the row (slice) direction. Alternatively, the X-ray detector 23 is a matrix-formed detector, namely, a two-dimensional array type detector (also referred to as a multi-slice type detector) having a plurality of channels in the channel direction and a plurality of rows of X-ray detecting elements in the slice direction. The X-ray detecting elements of the X-ray detector 23 detect X-rays applied from the X-ray tube 21.

The DAS 24 amplifies signals of transmission data detected by each X-ray detecting element of the X-ray detector 23 to convert the signals into digital signals. Output data from the DAS 24 is supplied to the image processing apparatus 12 through the controller 32 of the scanner 11.

The rotation portion 25 holds the X-ray tube 21, the diaphragm 22, the X-ray detector 23, and the DAS 24 as an integrated unit. The rotation portion 25 can rotate about the object O with the X-ray tube 21, the diaphragm 22, the X-ray detector 23, and the DAS 24 as an integrated unit and with the X-ray tube 21 and the X-ray detector 23 opposing each other. It is assumed that a direction parallel to a central axis of rotation of the rotation portion 25 is defined as a z axis direction, and a plane orthogonal to the z axis direction is defined as an x axis direction and a y axis direction.

The high voltage power supply 26 supplies the X-ray tube 21 with power required to apply X-rays in response to control of the controller 32.

The diaphragm driving device 27 has a mechanism of adjusting an irradiated range of X-ray on the diaphragm 22 in the slice direction and the direction normal to the slice direction under the control of the controller 33.

The rotation driving device 28 has a mechanism that allows, in response to control of the controller 32, the rotation portion 25 to rotate about a cavity space with a positional relationship of the rotation portion 25 maintained.

The table-top 30 is able to place the patient O on the top.

The table-top driving device 31 has a mechanism that, in response to control of the controller 32, moves the table-top 30 up and down along the y axis as well as backward and forward along the z axis. The rotation portion 25 has an opening in a central portion. The object O placed on the table-top 30 at the opening space enters the opening.

The controller 32 includes a CPU (central processing unit) and a memory. The controller 32 controls the X-ray detector 23, the DAS 24, the high voltage power supply 26, the diaphragm driving device 27, the rotation driving device 28, and the table-top driving device 31 to perform a scan.

The image processing apparatus 12 of the X-ray CT apparatus 1 has a computer-based configuration and can communicate with a network N such as a backbone LAN (local area network) in a hospital. The image processing apparatus 12 mainly includes basic hardware such as a CPU 41, a memory 42, an HDD (hard disc drive) 43, an inputting device 44, and a display device 45. The CPU 41 is interconnected to each of the hardware components constituting the image processing apparatus 12, via buses as common signal transmission lines. The image processing apparatus 12 may also include a storage medium drive 46.

The CPU 41 is a control device having a configuration of an integrated circuit (LSI) in which an electronic circuit composed of a semiconductor is housed in a package with multiple terminals. If an instruction is input by an operator such as a physician operating the inputting device 44, the CPU 41 executes a program stored in the memory 42. Alternatively, the CPU 41 loads a program stored in the HDD 43, a program transferred from the network N and installed in the HDD 43, or a program read out from a storage medium mounted on the storage medium drive 46 and installed in the HDD 43, into the memory 42 to execute such a program.

The memory 42 is a storage device such as ROM (read only memory) and RAM (random access memory). The memory 42 is used to store an IPL (initial program loading), a BIOS (basic input/output system), and data. Also, the main memory 42 is used as working memory for the CPU 41 and used to temporarily store data.

The HDD 43 is a storage device containing undetachable metal disks on which a magnetic substance is applied or evaporated. The HDD 43 is a storage device in which programs installed in the image processing apparatus 12 (including an application program as well as an OS (operating system)) and data such as projection data and image data are stored. Also, the OS may provide a GUI (graphical user interface) that makes heavy use of graphics for displaying information to the operator so that the operator can perform basic operations through the inputting device 44. Other than the HDD 43, storage devices such as an SSD and MRAM may also be used.

The inputting device 44 is a pointing device that can be operated by the operator and sends an input signal according to an operation to the CPU 41.

The display device 45 includes an image synthesis circuit, VRAM (video random access memory), and a display that are not shown. The image synthesis circuit generates synthetic data obtained by combining various parameters of character data and the like with image data. The VRAM develops synthetic data into data to be displayed on the display. The display is composed of a liquid crystal display, a CRT (cathode ray tube), or the like, and sequentially displays items of the developed data.

On the storage medium drive 46, a storage medium is detachably mounted. The storage medium drive 46 reads out data (including a program) stored in the storage medium, onto the bus. Also, the storage medium drive 46 writes data supplied via the bus into the storage medium. Such a storage medium can be provided in which so-called packaged software is stored.

The image processing apparatus 12 performs correction processing (preprocessing) such as logarithmic transformation processing and sensitivity correction on raw data input from the DAS 24 of the scanner 11 to generate projection data. Also, the image processing apparatus 12 performs scattered radiation removing processing on the preprocessed projection data. The image processing apparatus 12 removes scattered radiation based on values of projection data within an X-ray irradiated area. The image processing apparatus 12 performs scattered radiation correction by subtracting scattered radiation from target projection data, the scattered radiation being estimated by values of the target projection data or projection data adjacent thereto. The image processing apparatus 12 reconstructs the corrected projection data to generate and store image data.

Figure 2:
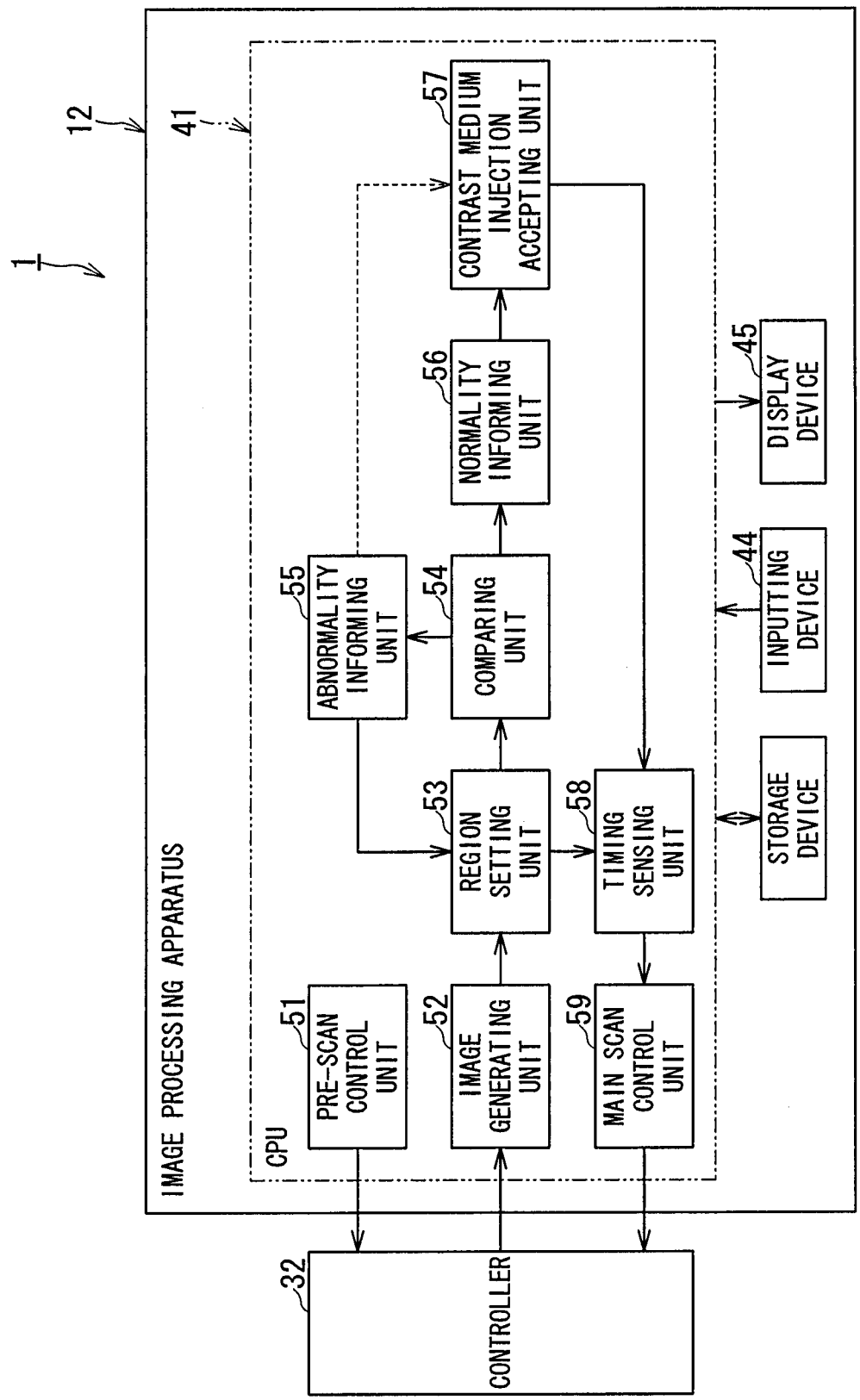
FIG. 2 is a block diagram illustrating functions of the X-ray CT apparatus according to the present embodiment.

FIG. 2 is a block diagram illustrating functions of the X-ray CT apparatus 1 according to the present embodiment.

The CPU 41 of the image processing apparatus 12 executes programs, whereby the X-ray CT apparatus 1 functions as a pre-scan control unit 51, an image generating unit 52, a region setting unit 53, a comparing unit 54, an abnormality informing unit 55, a normality informing unit 56, a contrast medium injection accepting unit 57, a timing sensing unit 58, and a main scan control unit 59, as shown in FIG. 2. All or a part of the components 51 to 59 of the X-ray CT apparatus 1 may also be provided in the X-ray CT apparatus 1 as hardware.

The pre-scan control unit 51 has a function to perform a pre-scan of a patient O before a main scan is performed in which a contrast medium agent is injected into the object, for example, a dynamic scan by controlling an operation of the scanner 11 through the controller 32. The pre-scan performed by the pre-scan control unit 51 may be a non-contrast scan, or a scan performed after a contrast medium agent is injected and before the agent reaches an ROI (region of interest). Hereinafter, it is assumed that the pre-scan performed by the pre-scan control unit 51 is a non-contrast scan. The pre-scan control unit 51 performs a conventional scan, a helical scan, a volume scan, and the like.

The image generating unit 52 has a function to generate N (N=1, 2, . . . ) slices of (axial) non-contrast image data on the basis of the data collected by the scanner 11 through the pre-scan performed in response to the control of the pre-scan control unit 51. If N is one, the image generating unit 52 generates single-sliced non-contrast image data. If N is equal to or greater than two, the image generating unit 52 generates multi-sliced non-contrast image data. The non-contrast image data generated by the image generating unit 52 is stored in a storage device such as the HDD 43.

The region setting unit 53 has a function to set an ROI for measurement of variation of a contrast medium agent using Real Prep on the basis of the non-contrast image data generated by the image generating unit 52. For example, the region setting unit 53 sets the ROI on the basis of an input signal input through the inputting device 44 by the operator viewing the non-contrast image data displayed on the display device 45.

Also, the region setting unit 53 has a function to set a larger region encompassing the set ROI and a region around the ROI (optionally including a region in the slice direction). The larger region is used for determining whether a high CT value region exists. The region setting unit 53 may automatically set the larger region based on the set ROI, or set the larger region based on an input signal input by the operator through the inputting device 44.

Figure 3:
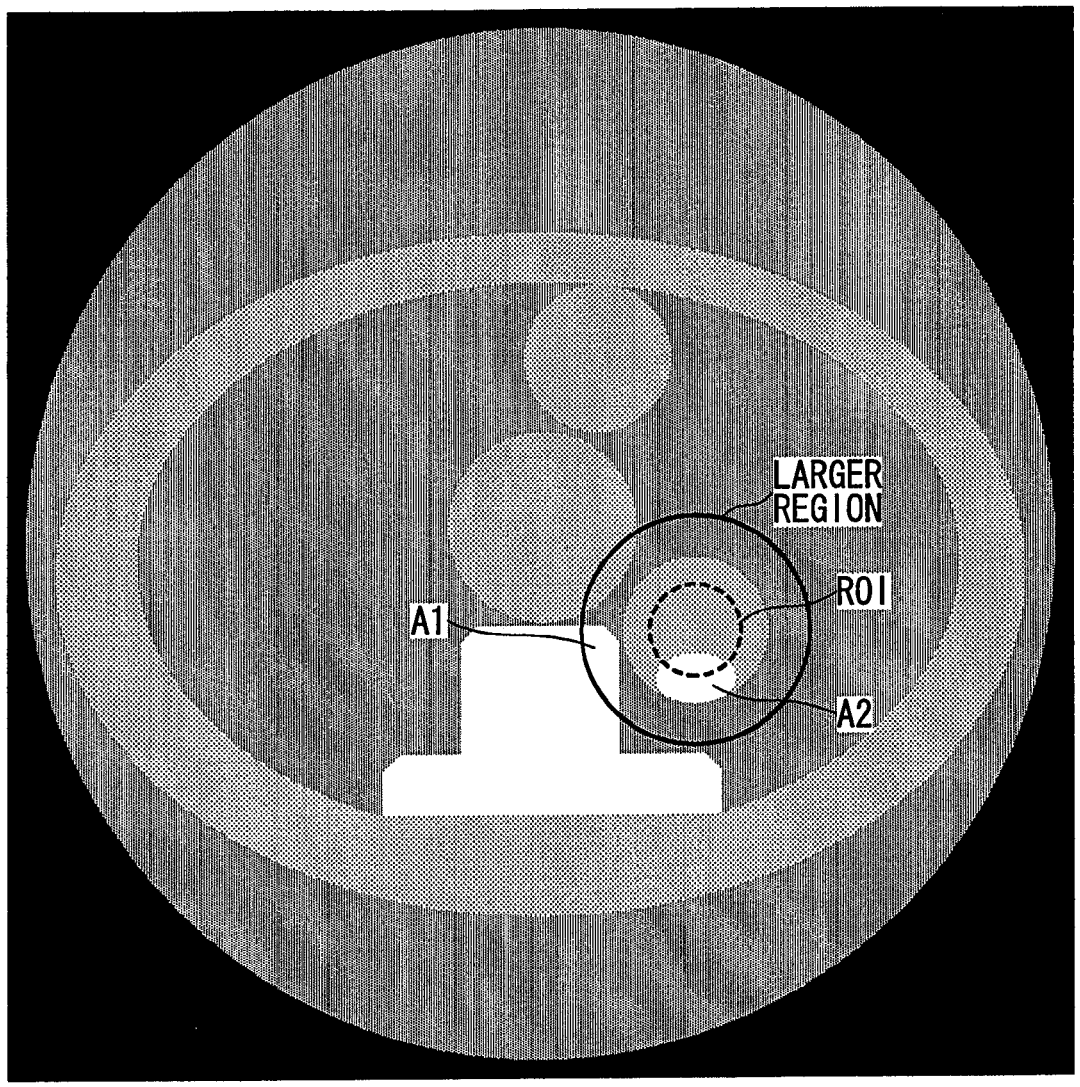
FIG. 3 is a diagram to explain a method for setting a larger region using single-sliced non-contrast image data.

FIG. 3 is a diagram to explain a method for setting the larger region using single-sliced non-contrast image data.

The operator designates the ROI on the basis of the non-contrast image data shown in FIG. 3. The region setting unit 53 sets the larger region so as to encompass the entire set ROI. It is assumed that the larger region includes high CT value regions A1 and A2.

Figure 4:
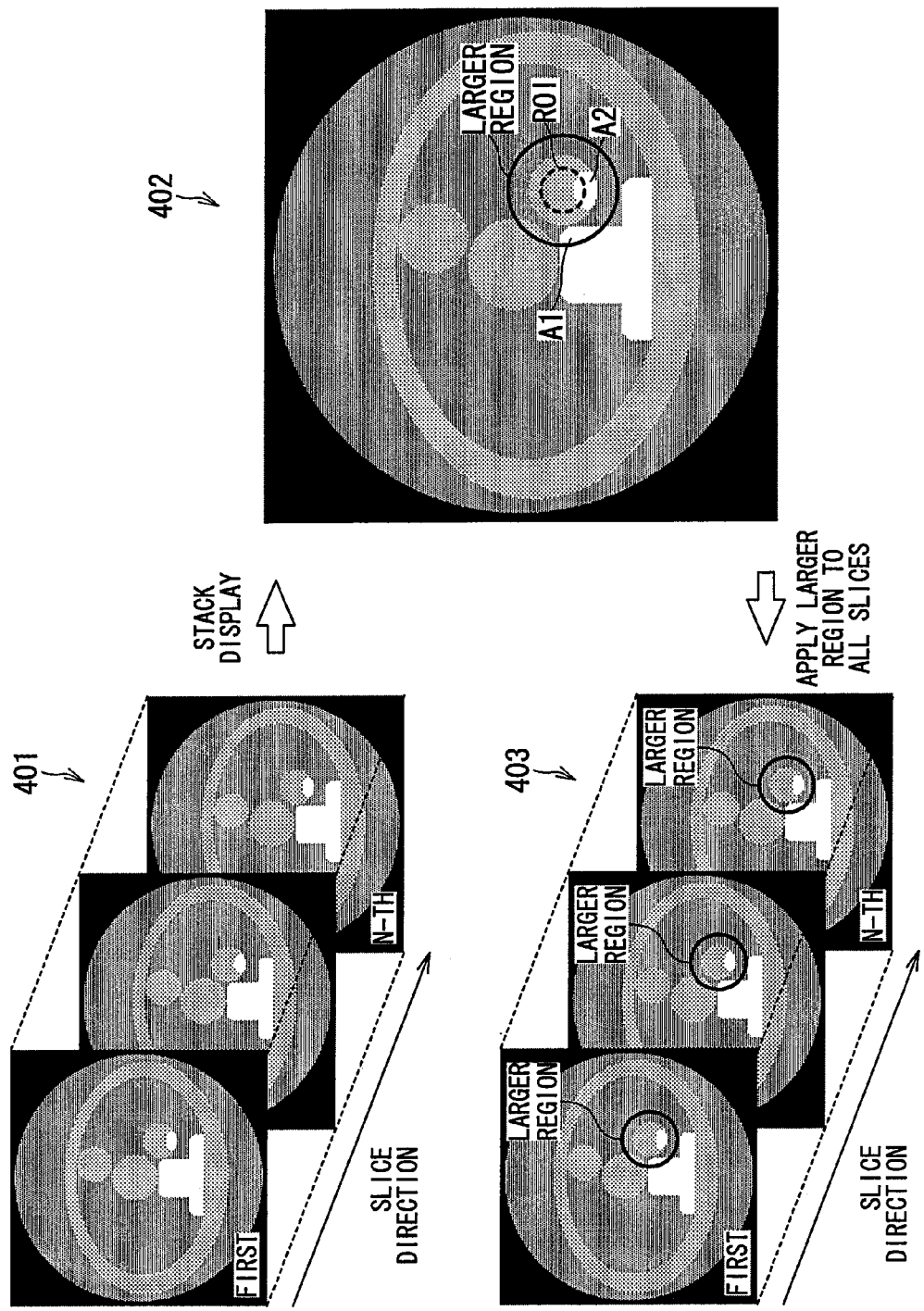
FIG. 4 is a diagram to explain a method for setting a larger region using multi-sliced non-contrast image data.

FIG. 4 is a diagram to explain a method for setting the larger region using multi-sliced non-contrast image data.

FIG. 4 shows multi-sliced non-contrast image data 401, 403, and non-contrast image data 402 stack-displayed based upon the multi-sliced non-contrast image data. The stack-displayed non-contrast image data 402 is generated by averaging at least a part of N slices of the non-contrast image data 401. FIG. 4 shows an example in which the stack-displayed non-contrast image data 402 is generated by averaging all the slices of the N slices of the non-contrast image data 401. Once the operator designates the ROI on the basis of the non-contrast image data 402, the region setting unit 53 sets the ROI on each of the non-contrast image data 402. Then, the region setting unit 53 sets the larger region on the non-contrast image data 402 so as to encompass the entire set ROI. It is now assumed that the larger region includes high CT value regions A1, A2.

Note that the region setting unit 53 is not limited to setting an ROI and a larger region using stack-displayed non-contrast image data. For example, if the operator selects an n-th (n=1, 2, . . . , N) slice of non-contrast image data from N slices of the non-contrast image data and designates the ROI on the basis of the selected n-th slice of the non-contrast image data, the region setting unit 53 sets the ROI on each of the N slices of the non-contrast image data. Alternately, if the operator selects an n-th slice of non-contrast image data and designates the ROI on the basis of the selected n-th slice of the non-contrast image data, the region setting unit 53 sets the ROI on each (n−i)-th to (n+i)-th slice of N slices of the non-contrast image data. Then, so as to encompass the entire ROI, the region setting unit 53 sets a larger region on each slice of the non-contrast image data on which the ROI is set.

The comparing unit 54 illustrated in FIG. 2 has a function to compare a CT value (pixel value) in the larger region set by the region setting unit 53 with a first threshold set for excluding the high CT value regions A1, A2, thereby determining whether or not the larger region includes a high CT value region. That is, the comparing unit 54 compares a CT value of a larger region including an ROI with the first threshold.

Now, a reason to determine whether a larger region includes a high CT value region is as follows: even if an existing high CT value region is outside an ROI at the time of setting the ROI, for example, after the injection of a contrast medium agent is started, the high CT value region may enter the ROI because of a heartbeat, breathing, and a body movement of an object, so that the timing of starting a main scan may be mistaken.

If it is determined that the larger region set by the region setting unit 53 includes a CT value higher than the first threshold on the basis of a comparison result from the comparing unit 54, as it is likely that the ROI includes a high CT value region or a high CT value region enters the ROI after the injection of the contrast medium agent is started, the abnormality informing unit 55 may have a function to inform the operator of the fact (an ROI abnormality). Similarly, in the case where the image generating unit 52 generates multi-sliced non-contrast image data, if it is determined that the larger region set by the region setting unit 53 includes a CT value higher than the first threshold based on a comparison result from the comparing unit 54, the abnormality informing unit 55 may inform the operator of the fact.

Abnormality information of an ROI may be output from a speaker (not shown) or output through the display device 45. If the abnormality information of the ROI is output from the display device 45, a CT value of the non-contrast image data, higher than the first threshold, may also be displayed in color depending upon the value. Once an ROI abnormality is informed by the abnormality informing unit 55, the region setting unit 53 is able to reset the ROI on the basis of the non-contrast image data generated by the image generating unit 52.

If it is determined that the larger region set by the region setting unit 53 does not include a CT value higher than the first threshold on the basis of a comparison result from the comparing unit 54, as it is unlikely (not likely) that the ROI includes a high CT value region or a high CT value region enters the ROI after the injection of the contrast medium agent is started, the normality informing unit 56 may have a function to inform the operator of the fact (an ROI normality). Similarly, in the case where the image generating unit 52 generates multi-sliced non-contrast image data, if it is determined that the larger region set by the region setting unit 53 does not include a CT value higher than the first threshold based on a comparison result from the comparing unit 54, the normality informing unit 56 may inform the operator of the fact.

The contrast medium injection accepting unit 57 may have a function to accept an instruction to start injecting a contrast medium agent in response to an input signal input by the operator through the inputting device 44 if the abnormality informing unit 55 or the normality informing unit 56 informs the operator of an abnormality/normality of an ROI. Even if an abnormality is informed by the abnormality informing unit 55, the operator may allow the execution of a main scan. For example, if the abnormality informing unit 55 displays in color the CT value of image data, higher than the first threshold, depending upon the value, the operator viewing the color display may make an instruction through the inputting device 44 to start injecting a contrast medium agent in preference to the reset of an ROI.

After the injection of the contrast medium agent into a patient O is started, the timing sensing unit 58 has a function to sense a timing of start (trigger) for the main scan, at which a CT value of the ROI set by the region setting unit 53 exceeds a preset second threshold after Real Prep is started after injection of the contrast medium agent into the patient is started.

Once the timing sensing unit 58 has function to sense a timing to start the main scan, the main scan control unit 59 controls an operation of the scanner 11 through the controller 32 to perform the main scan of the patient O.

The image generating unit 52 has a function to generate multiple slices of contrast image data based on data collected by the scanner 11 performing the main scan in response to the control of the main scan control unit 59. The contrast image data generated by the image generating unit 52 is stored in a storage device such as the HDD 43.

Next, an operation of the X-ray CT apparatus 1 according to the present embodiment will be described with reference to a flow chart shown in FIG. 5.

First, the X-ray CT apparatus 1 controls the operation of the scanner 11 through the controller 32 to perform a non-contrast pre-scan of a patient O before a main scan (step ST1). The X-ray CT apparatus 1 generates N slices of non-contrast image data based on the data collected by the scanner 11 through the pre-scan performed in response to the control of the pre-scan control unit 51 (step ST2). The non-contrast image data generated in step ST2 is stored in a storage device such as the HDD 43.

The X-ray CT apparatus 1 sets an ROI for measurement of variation of a contrast medium agent based on the non-contrast image data generated in step ST2 (step ST3). For example, in step ST3, the X-ray CT apparatus 1 sets an ROI based on an input signal input through the inputting device 44 by the operator viewing the non-contrast image data displayed on the display device 45. Also, the X-ray CT apparatus 1 sets a larger region encompassing the ROI set in step ST3 and a region around the ROI, and being used for determining whether a high CT value region exists (step ST4).

The X-ray CT apparatus 1 compares each CT value in the larger region set in step ST4 with a first threshold set for excluding the high CT value regions A1, A2 (step ST5). As a comparison result in step ST5, the X-ray CT apparatus 1 determines whether or not the larger region includes a CT value higher than the first threshold (step ST6). If yes in step ST6, that is, if the X-ray CT apparatus 1 determines that the larger region includes a CT value higher than the first threshold, the X-ray CT apparatus 1 informs the operator of an abnormality of the ROI (step ST7). If the abnormality of the ROI is informed in step ST7, the X-ray CT apparatus 1 determines whether to reset an ROI based on an input signal input by the operator through the inputting device 44 (step ST8). If yes in step ST8, that is, if the X-ray CT apparatus 1 determines to reset an ROI, the X-ray CT apparatus 1 sets an ROI again based on the non-contrast image data generated in step ST2 (step ST3).

On the other hand, if no in step ST6, that is, if the X-ray CT apparatus 1 determines that the larger region does not include a CT value higher than the first threshold, the X-ray CT apparatus 1 informs the operator of the normality of the ROI (step ST9).

If no in step ST8, that is, if the X-ray CT apparatus 1 determines not to reset an ROI, or after step ST9, the X-ray CT apparatus 1 accepts an instruction to start injecting the contrast medium agent, based on an input signal input by the operator through the inputting device 44 (step ST10). Once the X-ray CT apparatus 1 accepts the instruction to start the injection of the contrast medium agent in step ST10, the injection of the contrast medium agent into the patient O starts.

The X-ray CT apparatus 1 starts Real Prep after the contrast medium agent is injected into the patient O (step ST11). The X-ray CT apparatus 1 senses a timing to start the main scan, at which a CT value of the ROI set in step ST3 exceeds a preset second threshold (step ST12). Once the X-ray CT apparatus 1 senses a timing to start the main scan in step ST12, the X-ray CT apparatus 1 controls the operation of the scanner 11 through the controller 32 to perform the main scan of the patient O (step ST13).

The X-ray CT apparatus 1 generates multiple slices of contrast image data based on data collected by the scanner 11 performing the main scan in step ST13 (step ST14). The contrast image data generated in step ST14 is stored in a storage device such as the HDD 43.

Figure 6:
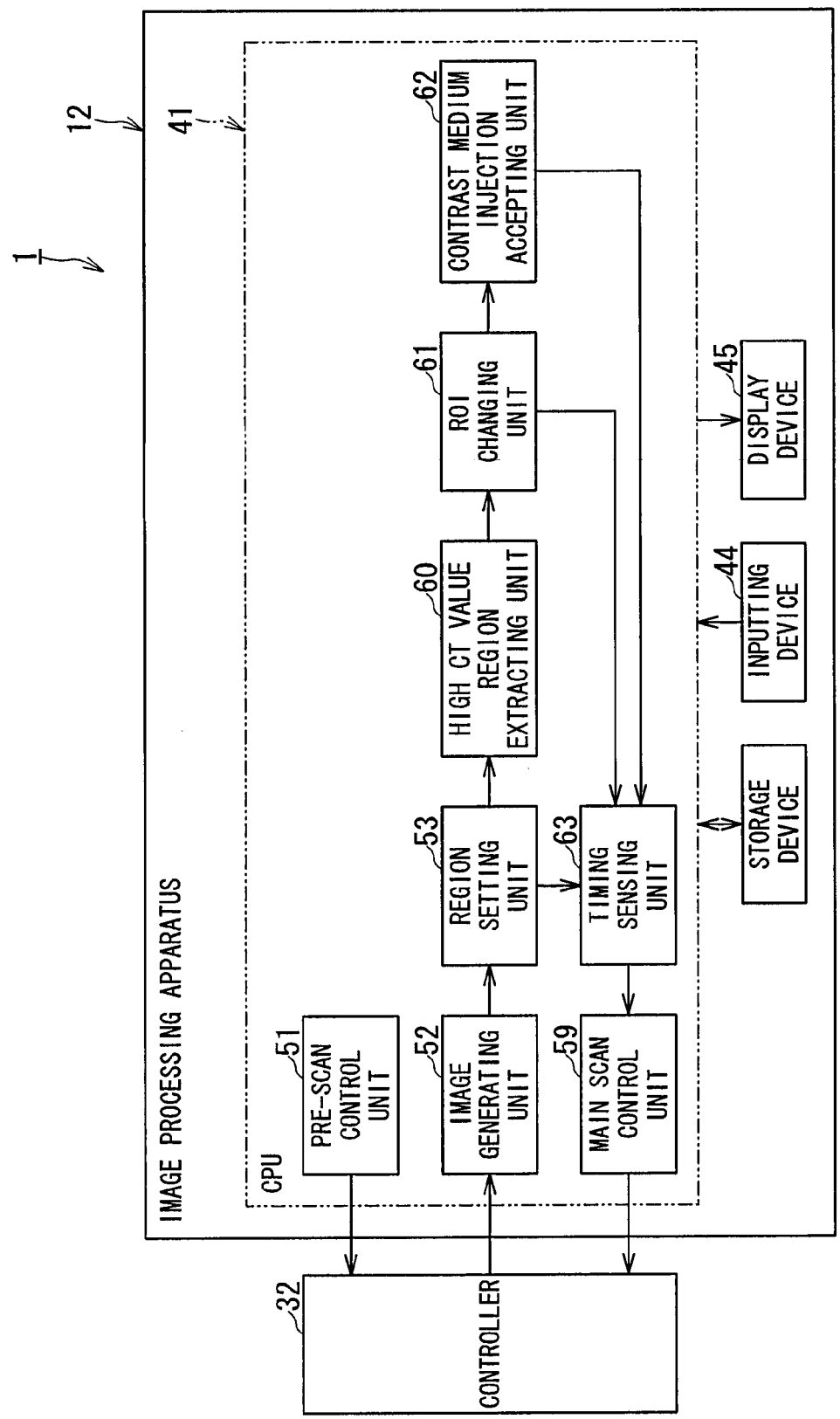
FIG. 6 is a block diagram illustrating a modified example of the functions of the X-ray CT apparatus according to the present embodiment.

FIG. 6 is a block diagram illustrating a modified example of the functions of the X-ray CT apparatus 1 according to the present embodiment.

The CPU 41 of the image processing apparatus 12 executes programs, and thereby the X-ray CT apparatus 1 functions, as shown in FIG. 6, as the pre-scan control unit 51, the image generating unit 52, the region setting unit 53, the main scan control unit 59, a high CT value region extracting unit 60, an ROI changing unit 61, a contrast medium injection accepting unit 62, and a timing sensing unit 63. All or a part of the components 51 to 53, and 59 to 63 of the X-ray CT apparatus 1 may be included as hardware in the X-ray CT apparatus 1.

In the X-ray CT apparatus 1 illustrated in FIG. 6, same reference numerals are used for denoting the same functions as those in the X-ray CT apparatus 1 illustrated in FIG. 2 and descriptions thereof are omitted.

The high CT value region extracting unit 60 compares each CT value of a larger region set by the region setting unit 53 with a first threshold set for excluding high CT value regions A1, A2, thereby extracting a high CT value region from the larger region.

If the high CT value region extracting unit 60 has a function to extract a high CT value region, the ROI changing unit 61 changes the ROI set by the region setting unit 53 so as not to include the high CT value region. For example, if a high CT value region is extracted, the ROI part setting unit 61 changes (modifies) the ROI so as not to include a region within a needed distance from the high CT value region. Also, for example, if a high CT value region is extracted, the ROI changing unit 61 shrinks the ROI so as not to include a region within a needed distance from the high CT value region. Further, for example, if a high CT value region is extracted, the ROI changing unit 61 changes (moves) a position of the ROI so as not to include a region within a needed distance from the high CT value region.

Figure 7A:
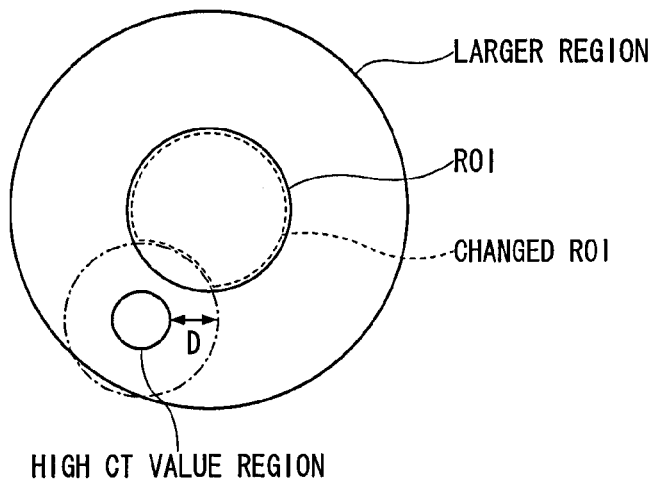
FIGS. 7A to 7C are diagrams to explain changing of ROIs.
Figure 7B:
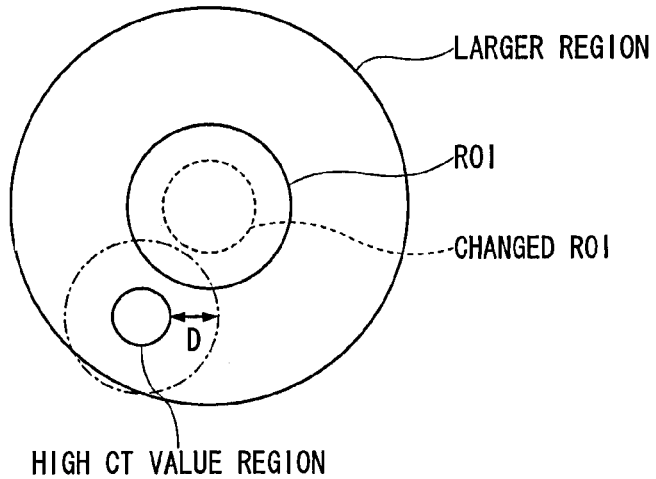
Figure 7C:
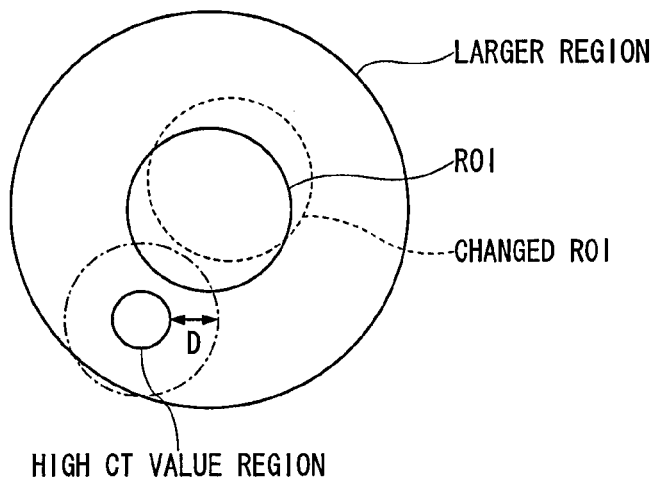

FIGS. 7A to 7C are diagrams for illustrating changing of ROIs.

FIG. 7A shows an example in which if a high CT value region is extracted, an ROI is changed so as not to include a region within a needed distance D from the high CT value region. According to FIG. 7A, shape of the ROI is changed.

FIG. 7B shows an example in which if a high CT value region is extracted, an ROI is shrunk so as not to include a region within a needed distance D from the high CT value region.

FIG. 7C shows an example in which if a high CT value region is extracted, a position of an ROI is changed so as not to include a region within a needed distance D from the high CT value region. According to FIG. 7C, the position of the ROI is moved.

A high CT value region outside and around an ROI may enter the ROI because of a heartbeat, breathing, and a body movement of the object after the injection of a contrast medium agent is started. Thus, the ROI changing unit 61 defines a region within a needed distance D from a high CT value region outside and around the ROI as a movement estimated region of the high CT value region and changes a position of the ROI so as not to include the movement estimated region.

It should be noted that the changing of ROIs shown in FIGS. 7A to 7C may be made singly or in combination.

Once the ROI changing unit 61 changes an ROI or the ROI changing unit 61 determines that changing an ROI is unnecessary, the contrast medium injection accepting unit 62 illustrated in FIG. 6 has a function to accept an instruction to start the injection of a contrast medium agent based on an input signal input by the operator through the inputting device 44.

The timing sensing unit 63 has a function to sense a timing to start the main scan, at which a CT value of the ROI changed by the ROI changing unit 61 or the ROI set by the region setting unit 53 exceeds a preset second threshold after Real Prep is started after the injection of the contrast medium agent into the patient O is started.

Next, the modified example of the operation of the X-ray CT apparatus 1 according to the present embodiment will be described with reference to a flow chart shown in FIG. 8.

Figure 5:
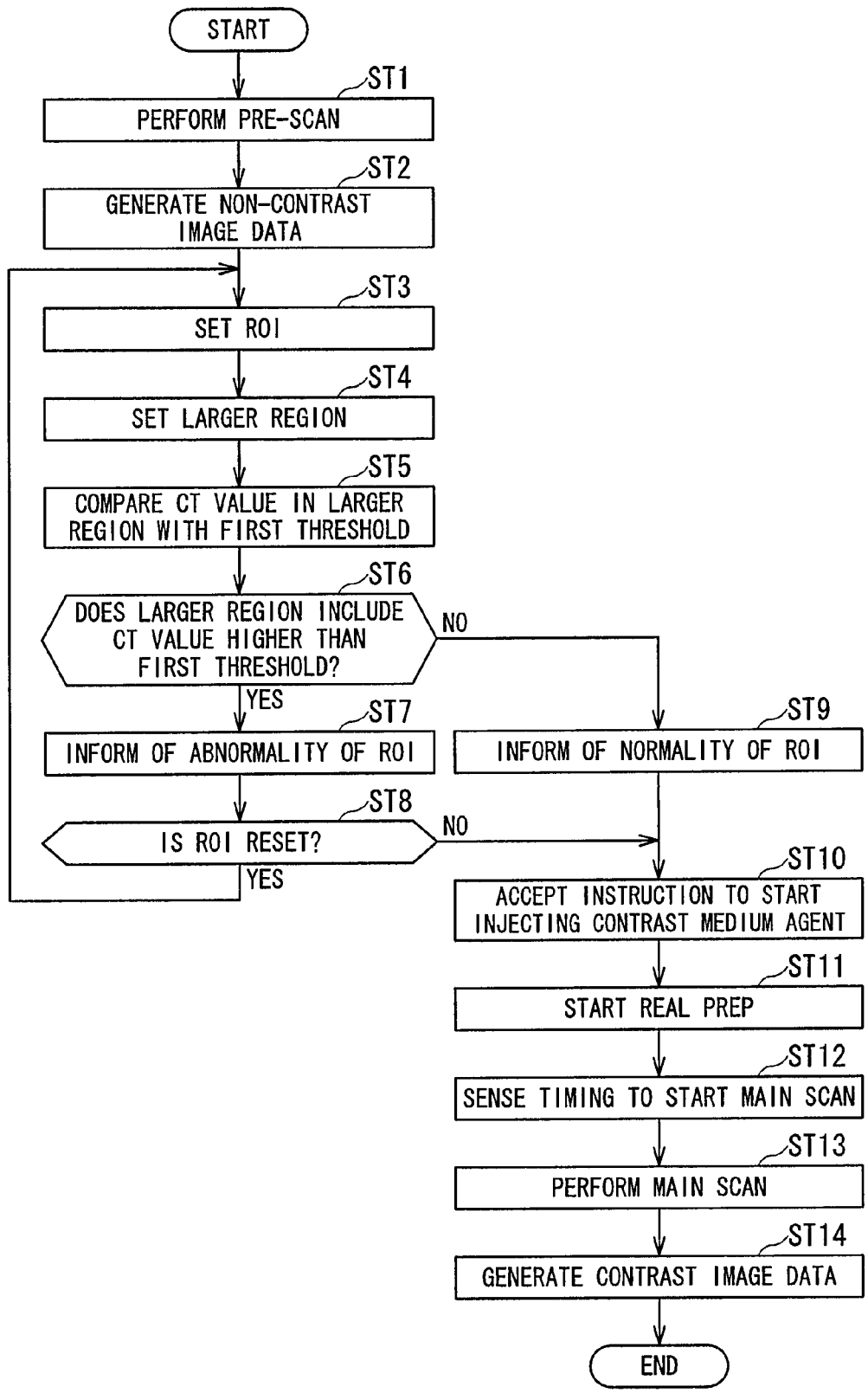
FIG. 5 is a flow chart showing an operation of the X-ray CT apparatus according to the present embodiment.
Figure 8:
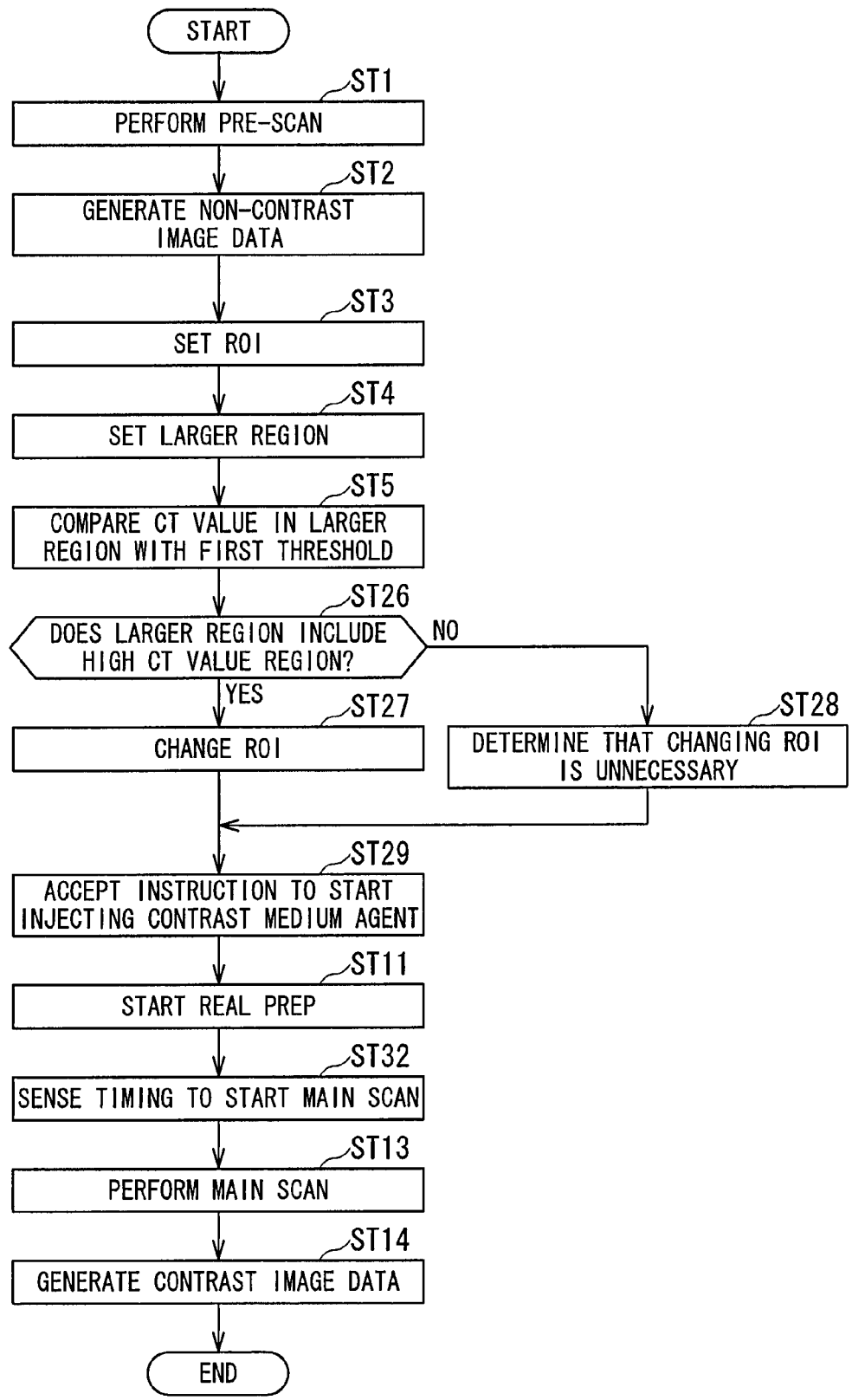
FIG. 8 is a flow chart showing the modified example of the operation of the X-ray CT apparatus according to the present embodiment.

In the operation shown in FIG. 8, performed by the X-ray CT apparatus 1, same reference numerals are used for denoting the same steps as that shown in FIG. 5, performed by the X-ray CT apparatus 1, and descriptions thereof are omitted.

The X-ray CT apparatus 1 compares each CT value in the larger region set in step ST4 with a first threshold set for excluding the high CT value regions A1, A2 (step ST5), thereby determining whether or not the larger region includes a high CT value region (step ST26). If yes in step ST26, that is, if determining that the larger region includes a high CT value region, the X-ray CT apparatus 1 changes the ROI set in step ST3, based on the high CT value region (step ST27). A method for changing an ROI in step ST27 is, for example, according to FIGS. 7A to 7C.

On the other hand, if no in step ST26, that is, if determining that the larger region does not include a high CT value region, the X-ray CT apparatus 1 determines that changing the ROI set in step ST3 is unnecessary (step ST28).

If the ROI is changed in step ST27, or if it is determined that changing the ROI is unnecessary in step ST28, the X-ray CT apparatus 1 accepts an instruction to start the injection of a contrast medium agent based on an input signal input by the operator through the inputting device 44 (step ST29). Once the X-ray CT apparatus 1 accepts the instruction to start the injection of the contrast medium agent in step ST29, the injection of the contrast medium agent into the patient O starts.

The X-ray CT apparatus 1 starts Real Prep after the contrast medium agent is injected into the patient O (step ST11). The X-ray CT apparatus 1 senses a timing to start the main scan, at which a CT value of the ROI changed in step ST27 or a CT value of the ROI set in step ST3 exceeds a preset second threshold (step ST32). If sensing the timing to start the main scan in step ST32, the X-ray CT apparatus 1 controls the operation of the scanner 11 through the controller 32 to perform the main scan of the patient O (step ST13).

According to the X-ray CT apparatus 1 of the present embodiment, since the presence of a high CT value region is determined based on non-contrast image data, not in an ROI, but in a larger region encompassing the ROI and a region around the ROI, even if a heartbeat, breathing, or a body movement of a patient O occurs after the injection of a contrast medium agent is started, a timing to start the main scan can be correctly and accurately sensed.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray computed tomography (CT) apparatus, comprising:
    a scanner including an X-ray source and an X-ray detector to collect data of an object; and
    processing circuitry configured to:
        control an operation of the scanner to perform a pre-scan;
        generate image data of the object based upon the pre-scan;
        set, based on the generated image data, a region of interest, which includes a target site, and set a larger region encompassing the region of interest and a region around the set region of interest; and
        determine a timing to start a main scan based on a time when a pixel value in the region of interest exceeds a second threshold after injection of a contrast agent is started, the injection being started if no pixel in the larger region exceeds a first threshold.

2. The X-ray CT apparatus according to claim 1, wherein the processing circuitry is further configured to, when the timing to start the main scan is determined, control an operation of the scanner to perform the main scan.

3. The X-ray CT apparatus according to claim 1, wherein the processing circuitry is further configured to, when the larger region includes a pixel value higher than the first threshold, provide information that the larger region includes the pixel value.

4. The X-ray CT apparatus according to claim 3, wherein the processing circuitry is further configured to, when the larger region does not include the pixel value higher than the first threshold, provide information that the larger region does not include the pixel value.

5. The X-ray CT apparatus according to claim 1, wherein the processing circuitry is further configured to:
    when the larger region includes a pixel value region higher than the first threshold, change the region of interest so as not to include the pixel value region; and determine the timing based on the changed region of interest.

6. The X-ray CT apparatus according to claim 5, wherein the processing circuitry is further configured to, when the pixel value region exists, modify the region of interest so as not to include a region within a needed distance from the pixel value region.

7. The X-ray CT apparatus according to claim 5, wherein the processing circuitry is further configured to, when the pixel value region exists, shrink the region of interest so as not to include a region within a needed distance from the pixel value region.

8. The X-ray CT apparatus according to claim 5, wherein the processing circuitry is further configured to, when the pixel value region exists, move a position of the region of interest so as not to include a region within a needed distance from the pixel value region.

9. The X-ray CT apparatus according to claim 1, further comprising:
    a display device configured to, when the larger region includes a pixel value higher than the first threshold, display in color, pixel values of the image data including the pixel value higher than the first threshold depending upon the pixel value; and
    an inputting device configured to, after the display in color, receive an input from an operator to provide the processing circuitry with an instruction to determine the timing to start the main scan.

10. The X-ray CT apparatus according to claim 1, further comprising:
    a display device configured to, when the processing circuitry generates multi-sliced image data, stack-display all slices of the image data; and
    an inputting device configured to designate the region of interest in the stack-displayed image data,
    wherein the processing circuitry is further configured to set the designated region of interest to each of all the slices of the image data and set the larger region to each of all the slices of the image data so as to encompass an entire set region of interest.

11. The X-ray CT apparatus according to claim 1, further comprising:
    a display device configured to, when the processing circuitry generates multi-sliced image data, stack-display a part of slices of the multi-sliced image data; and
    an inputting device configured to designate the region of interest to the stack-displayed image data,
    wherein the processing circuitry is further configured to set the designated region of interest to each of the part of the slices of the image data and set the larger region to each of the part of the slices of the image data so as to encompass an entire set region of interest.

12. The X-ray CT apparatus according to claim 1, further comprising:
    a display device configured to, when the processing circuitry generates multi-sliced image data, select one slice of image data from the multi-sliced image data and display the selected image data; and
    an inputting device configured to designate the region of interest to the displayed image data,
    wherein the processing circuitry is further configured to set the designated region of interest to each of all slices of the image data and set the larger region to each of all the slices of the image data so as to encompass an entire set region of interest.

13. The X-ray CT apparatus according to claim 1, further comprising:
    a display device configured to, when the image generating unit generates multi-sliced image data, select one slice of image data from the multi-sliced image data and display the selected image data; and an inputting device configured to designate the region of interest to the displayed image data, wherein the processing circuitry is further configured to set the designated region of interest to each of a part of slices of the multi-sliced image data including the selected image data as a center of the part of the slices of the image data, and set the larger region to each of the part of the slices of the image data so as to encompass an entire set region of interest.

14. An image processing method, comprising:

performing a pre-scan by controlling an operation of a scanner that includes an X-ray source and an X-ray detector to collect data of an object;

generating image data of the object based upon the pre-scan;

setting, based on the generated image data, a region of interest, which includes a target site, and setting a larger region encompassing the set region of interest and a region around the region of interest;

and determining a timing to start a main scan based on a time when a pixel value in the region of interest exceeds a second threshold after injection of a contrast agent is started, the injection being started if no pixel in the larger region exceeds a first threshold.

* * * * *